(12) United States Patent
Kirkor et al.

(10) Patent No.: US 7,097,788 B2
(45) Date of Patent: Aug. 29, 2006

(54) CONDUCTING INKS

(75) Inventors: Ewa Stanislawa Kirkor, Bradford, CT (US); April Dawn Schricker, Austin, TX (US); Alexander Scheeline, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 242 days.

(21) Appl. No.: 10/610,363

(22) Filed: Jun. 30, 2003

(65) Prior Publication Data

US 2004/0262582 A1    Dec. 30, 2004

(51) Int. Cl.
*H01B 1/24* (2006.01)

(52) U.S. Cl. .................. 252/502; 252/512; 427/355; 427/369

(58) Field of Classification Search .......... 252/500, 252/502, 511, 512; 427/331, 355, 369
See application file for complete search history.

(56) References Cited

U.S. PATENT DOCUMENTS

| | | | |
|---|---|---|---|
| 4,035,265 A | 7/1977 | Saunders | |
| 4,628,334 A | 12/1986 | Dagna et al. | |
| 4,911,794 A | 3/1990 | Parce et al. | |
| 4,919,141 A | 4/1990 | Zier et al. | |
| 5,114,477 A | 5/1992 | Mort et al. | |
| 5,174,925 A | 12/1992 | Fujii et al. | |
| 5,411,647 A | 5/1995 | Johnson et al. | |
| 5,445,998 A | 8/1995 | Zimmer | |
| 5,476,776 A | 12/1995 | Wilkins | |
| 5,671,029 A * | 9/1997 | Haruki | 349/96 |
| 5,704,118 A | 1/1998 | Kaneko et al. | |
| 5,770,028 A | 6/1998 | Maley et al. | |
| 5,780,101 A | 7/1998 | Nolan et al. | |
| 5,843,342 A | 12/1998 | Ehrreich | |
| 5,891,398 A | 4/1999 | Lewis et al. | |
| 5,897,813 A | 4/1999 | Titomir et al. | |
| 5,916,642 A | 6/1999 | Chang | |
| 6,157,427 A * | 12/2000 | Saynor et al. | 349/123 |
| 6,315,395 B1 | 11/2001 | Imai | |
| 6,405,066 B1 | 6/2002 | Essenpreis et al. | |
| 6,631,710 B1 | 10/2003 | Schultheis | |

FOREIGN PATENT DOCUMENTS

| | | |
|---|---|---|
| WO | WO 96/06947 | 3/1996 |
| WO | WO 96/17025 | 6/1996 |
| WO | WO 02/05294 | 1/2002 |

OTHER PUBLICATIONS

Choi et al "Fully sealed, high-brightness carbon nanotube filed-emission display", Applied Physica Lett. 75(20), 3129-3131 (1999).*

Choi et al "Carbon nanotubes for full-color filed emission displays", JJAP, Part 1, 39(5A), Abstract. (2000).*

Ajayan et al., "Capillarity-Induced Filling of Carbon Nanotubes," Nature, 1993, pp. 333-334, vol. 361.

Bard et al., "Controlled Potential Microelectrode Techniques-Potential Step Methods," Chapter 5 of Electrochemical Methods Fundamentals and Applications, 1980, pp. 136-206.

(Continued)

*Primary Examiner*—Mark Kopec
(74) *Attorney, Agent, or Firm*—Evan Law Group LLC

(57) ABSTRACT

A method of increasing conductivity of an ink, comprises orienting particles in the ink. The ink comprises the particles and solvent, and the particles are conductive anisotropic particles.

3 Claims, 3 Drawing Sheets

OTHER PUBLICATIONS

Barnes et al., "As-Spun Orientation as an Indication of Graphitized Properties of Mesophase-Based Carbon Fiber," Carbon, 1998, pp. 855-860, vol. 36.

Bartlett et al., "Approaches to the Integration of Electrochemistry and Biotechnology II. The Horseradish Peroxidase Catalyzed Oxidation of 2,4,6-trimethylphenol by Electrogenerated Hydrogen Peroxide," J. Electrochem. Soc., 1999, pp. 1088-1092, vol. 146.

Bartlett et al., "An Enzyme Switch Employing Direct Electrochemical Communication Between Horseradish Peroxidase and a Poly(aniline) Film," Analytical Chem., 1998, pp. 3685-3693, vol. 70.

Borchardt et al., "Disposable Ion-Selective Electrodes," Sensors and Actuators B, 1995, pp. 721-723, vols. 24-25.

Borchardt et al., "Disposable Sodium Electrodes," Talania, 1994, pp. 1025-1028, vol. 41.

Brillion, "Brillion™ Conductive Ink Technology," obtained from http://www.colortronics.com/brillion/htm, 2002.

Celzard et al., "Anisotropic Percolation in an Epoxy—Graphite Disc Composite," Solid State Communications, 1994, pp. 377-393, vol. 92.

Conductive Compounds, Inc., obtained from http://www.conductivecompounds.com/products.html, 2002, 2 pages.

Crowley et al., "Experimental and Theroretical Studies of a Coupled Chemical Oscillator: Phase Death, Multistability, and In-Phase and Out-of-Phase Entrainment," J. Physical Chem., 1989, pp. 2496-2502, vol. 93.

Dani et al., "Electrical Percolation Behavior of Short-Fiber Composites: Experimental Characterization and Modeling," Composites Science and Technology, 1996, pp. 911-920, vol. 56.

Davis et al., "Protein Electrochemistry at Carbon Nanotube Electrodes," J. Electroanalytical Chem., 1997, pp. 279-282, vol. 440.

Dieckmann et al., "Disposable Reference Electrode," Sensors and Actuators B-Chemical, 1995, pp. 276-278, vols. 24 and 25.

Dumschat et al., "Potentiometric Test Strip," Sensors and Actuators B, 1995, pp. 279-281, vols. 24-25.

Ebbesen, "Wetting, Filling and Decorating Carbon Nanotubes," J. Phys. Chem. Solids, 1996, pp. 951-955, vol. 57.

Fan et al., "Synthesis and Properties of Carbon Nanotube-Polypyrrole Composites," Synthetic Metals, 1999, pp. 1266-1267, vol. 102.

Fisher, Introduction to Electrode Dynamics, 1996, pp. 1-25.

Flandin et al., "Anomalous Percolation Transition in Carbon-Black-Epoxy Composite Materials," Am. Physical Soc., Physical Review B, 1999, pp. 14349-14355, vol. 59.

Freemantle, "Filled Carbon Nanotubes Could Lead to Improved Catalysts and Biosensors," Science/Technology, 1996, pp. 62-66.

Ge et al., "Simultaneous Determination of Maltose and Glucose Using a Screen-Printed Electrode System," Biosensors & Bioelectronics, 1998, pp. 333-339, vol. 13.

Ge et al., "Potassium Ferricyanide Mediated Disposable Biosensor for Determination of Maltose and Glucose," Physical Letters, 1998, pp. 383-395, vol. 31.

Hermes et al., "An Amperometric Microsensor Array with 1024 Individually Addressable Elements for Two-Dimensional Concentration Mapping," Sensors and Actuators B, 1994, pp. 33-37, vol. 21.

Hernadi et al., "Carbon Nanotube Formation Over Supported Catalysts," Molecular Crystals & Liquid Crystals Science & Technology Section A, Molecular Crystals & Liquid Crystals, 1998, pp. 179-184, vol. 310.

Hinkers et al., "An Amperometric Microsensor Array with 1024 Individually Addressable Elements for Two-Dimensional Concentration Mapping," Sensors and Actuators B, 1995, pp. 300-303, vols. 24-25.

Johnson et al., "Growth and Form of Gold Nanorods Prepared by Seed-Mediated, Surfactant-Directed Synthesis," J. Mater. Chem., 2002, pp. 1765-1770, vol. 12.

Kissinger et al., "Introduction to Analog Instrumentation," Chapter 6 of Laboratory Techniques in Electroanalytical Chemistry, 1996, pp. 165-194.

Knoll et al., "Microfibre Matrix-Supported Ion-Selective PVC Membranes," Sensors and Actuators B, 1994, pp. 1-5, vol. 20.

Kotov et al., "Ultrathin Graphite Oxide-Polyelectrolyte Composites Prepared by Self-Assembly: Transition Between Conductive and Non-Conductive States," Advanced Materials, 1996, pp. 637-641, vol. 8.

Lindgren et al., "Comparison of Rotating Disk and Wall Jet Electrode Systems for Studying the Kinetics of Direct and Mediated Electron Transfer for Horseradish Peroxidase on a Graphite Electrode," J. Electroanalytical Chem., 1998, pp. 113-120, vol. 458.

Lvovich et al., "Amperometic Sensors for Simultaneous Superoxide and Hydrogen Peroxide Detection," Analytical Chem., 1997, pp. 454-462, vol. 69.

Lvovich et al., "Simultaneous Superoxide and Hydrogen Peroxide Detection in Peroxidase/NADH Oscillator," Analytica Chimica Acta, 1997, pp. 315-323, vol. 354.

Martin et al., "Chemically Modified Electrodes," Chapter 13 of Laboratory Techniques in Electroanalytical Chemistry, 1996, pp. 403-442.

Mclachlan et al., "Analytic Scaling Functions Applicable to Dispersion Measurements in Percolative Metal-Insulator Systems," Am. Physical Soc., Physical Review B, 1998, pp. 13558-13564, vol. 58.

Michael et al., "Microelectrodes," Chapter 12 of Laboratory Techniques in Electroanalytical Chemistry, 1996, pp. 367-402.

Mroz et al., "Disposable Reference Electrode," Analyst., 1998, pp. 1373-1376, vol. 123.

Noy, "For Large . . . Fast . . . or Short-Run Applications: Isn't Piezo Grand?," SGIA Journal, First Quarter 1999, pp. 31-33.

Rao et al., "Synthesis of Multi-Walled and Single-Walled Nanotubes, Aligned-Nanotube Bundles and Nanorods by Employing Organometallic Precursors," Materials Res. Innovations, 1998, pp. 128-141, vol. 2.

Runnels et al., "Effects of pH and Surface Functionalities on the Cyclic Voltammetric Responses of Carbon-Fiber Microelectrodes," Analytical Chem., 1999, pp. 2782-2789, vol. 71.

Samanta et al., "Fiber Structure Study by Polarized Infrared Attentuated Total Reflection Spectroscopy," Applied Spectroscopy, 1990, pp. 286-289, vol. 44.

Schricker, "Probe Fabrication with the Intent to Solve the Question of Heterogeneity in the HRP Oscillatory Reaction," 1999, pp. 1-16.

Subramoney, "Novel Nanocarbons-Structure, Properties, and Potential Applications," Adv. Mater., 1998, pp. 1157-1171, vol. 10.

Tang et al., "Preparation, Alignment, and Optical Properties of Soluble Poly(phenylacetylene)-Wrapped Carbon Nanotubes," Macromolecules, 1999, pp. 2569-2576, vol. 32.

Tatsuma et al., "Enzyme Monolayer- and Bylayer- Modified Tin Oxide Electrodes for Determination of Peroxide and Glucose," Analytical Chem., 1989, pp. 2352-2355, vol. 61.

Tatsuma et al., "Kinetic Analysis of Electron Transfer from a Graphite Coating to Horseradish Peroxidase," J. Electroanalytical Chem., 1998, pp. 205-209, vol. 446.

Tchmutin et al., "Electrical Transport in 0-3 Epoxy Resin-Barium Titanate-Carbon Black Polymer Composites," J. Polymer Science: Part B: Polymer Physics, 1998, pp. 1847-1856, vol. 36.

Terrones et al., "Nanotubes: A Revolution in Materials Science and Electronics," Fullerenes and Related Structures, 1999, pp. 189-234, vol. 199.

Vanyesk, "Modern Techniques in Electroanalysis," Chemical Analysis Series, 1996, pp. 242-275, vol. 139.

Viswanathan et al., "Direct Imaging of the Percolation Network in a Three-Dimensional Disordered Conductor-Insulator Composite," Physical Review Letters, 1995, pp. 4433-4437, vol. 75.

Weber et al., "Estimation of the Volume Resistivity of Electrically Conductive Composites," Polymer Composites, 1997, pp. 710-725, vol. 18.

Zhu et al., "Nanostructure of GaN and SiC Nanowires Based on Carbon Nanotubes," J. Mater. Res., 1999, pp. 1175-1177, vol. 14.

Epoxies, Etc., "Electrically Conductive Ink", obtained from http://www.screenweb.com/industrial/prods/graphic990611g.html, pp. 1, (2002).

* cited by examiner

Rubbing Direction

CONDUCTING INKS

FEDERALLY SPONSORED RESEARCH OR DEVELOPMENT

This invention was made with Government support under Contract Number CHE96-15739 awarded by the National Science Foundation (NSF). The Government may have certain rights in the invention.

BACKGROUND

The use of carbon-based inks is known for the manufacture of carbon-based conductors, for example printed circuits and electrodes for sensors. In general, a carbon-based ink is an ink containing a carbon particulate such as graphite, amorphous carbon or a fullerene, suspended in a binder and a solvent. These inks are applied on a surface via a number of deposition techniques, including painting on with a brush, syringe application, and screen printing. The ink is allowed to dry and the resulting carbon-coated surface is subjected to a treatment at temperatures ranging from 50° C. to several hundred degrees Celsius. This high temperature treatment, or curing, is necessary to attain high conductivity in the resulting composite conductors.

The high temperatures needed for curing can limit the usefulness of carbon-based inks. The growing field of enzymatic electrochemical sensors is a case in point. In this type of sensor, a sensing electrode specific to a given analyte is made by linking or adsorbing a redox enzyme specific to the analyte of interest to a conductive surface. When the analyte is present in the sample being tested, electron transfer occurs and an electric signal proportional to the concentration of the analyte is thus generated. Examples include those described in U.S. Pat. Nos. 5,411,647; 5,476,776; 4,919,141; and 4,911,794. The sensor can also include an electron-transfer mediator that enhances the sensitivity of the system.

The enzyme typically is not incorporated in the ink, since it would denature and lose its activity during curing of the ink to increase the conductivity. This curing is necessary in order to optimize electron exchange between inks and enzymes. Thus, the sensor usually is manufactured by first applying and curing the carbon ink, and then the enzyme is adsorbed to the ink by immersion of the latter in a solution of the former.

One flexible and low cost way to manufacture these sensors would be by printing with a continuous ink-jet printer. However, the large particle size of the carbon particulate in the inks precludes their use in typical ink-jet printers. Thus, computers and peripherals typically cannot be used for flexible and low cost printing.

SUMMARY

In a first aspect, the present invention is a method of increasing conductivity of an ink, comprising orienting particles in the ink. The ink comprises the particles and solvent, and the particles are conductive anisotropic particles.

In a second aspect, the present invention is a method of increasing conductivity of an ink, comprising stretching a substrate. The ink comprises conductive anisotropic particles and a solvent, and the ink is on the substrate.

In a third aspect, the present invention is a method of increasing conductivity of an ink, comprising rubbing the ink. The ink comprises conductive anisotropic particles, and a solvent, and the ink is on a substrate.

In a fourth aspect, the present invention is a method of increasing conductivity of an ink, comprising applying an electric potential to the ink. The ink comprises conductive anisotropic particles, and a solvent, and the ink is on a substrate.

In a fifth aspect, the present invention a conductive ink, comprising conductive anisotropic particles and a solvent. The particles orient as the solvent evaporates.

In a sixth aspect, the present invention is an ink for manufacturing electrodes for enzymatic electrochemical sensors, comprising an enzyme, conductive anisotropic particles, and a solvent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
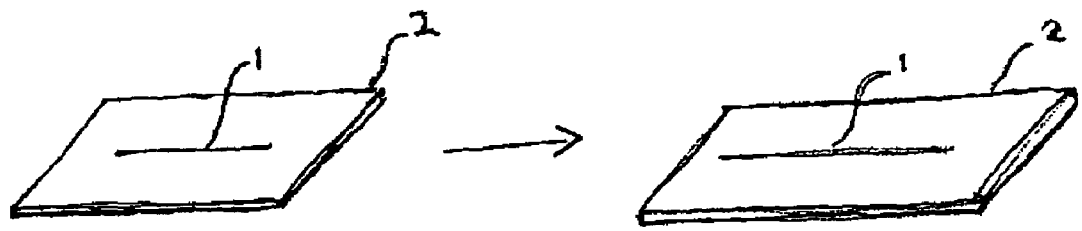
FIG. 1 illustrates the process of increasing the conductivity of an ink by substrate stretching.

The present invention makes use of new techniques for increasing the conductivity of inks containing conductive anisotropic particles without high temperature curing. This allows the incorporation of an enzyme in ink as a viable material for manufacturing electrochemical enzymatic sensors. This new method for manufacturing this type of sensors is simpler and lower in cost, as compared to other methods. In addition, the use of carbon-based ink compositions containing nanotubes or nanorods further allows implementation with ink-jet printers, thus increasing flexibility and further lowering costs.

In order to increase conductivity, a treatment, such as rubbing or stretching, is applied to an ink containing conductive anisotropic particles. One possible explanation for why this treatment increases conductivity is that this treatment induces orientation of the conductive anisotropic particles in the ink, thus facilitating electron flow.

The ink is prepared by suspending conductive anisotropic particles in a binder and solvent mixture. The ink may also contain other ingredients, for example surfactants, viscosity modifiers, and dyes or pigments. Furthermore, the binder is also optional. The particles may be a form of elemental carbon, such as graphite, carbon fibers and nanotubes, wherein a nanotube is a hexagonal lattice of carbon rolled into a cylinder (a nanotube is defined by its diameter, length, and chirality, or twist. Besides having a single cylindrical wall (single wall nanotubes, or SWNTs), nanotubes can have multiple walls (multiple wall nanotubes, or MWNTs)—cylinders inside the other cylinders). The particles may also be anisotropic metallic particles, for instance gold, silver, copper and nickel nanorods (Johnson et al., J. Mater. Chem., 2002, Vol. 12, pp. 1765–1770). Anisotropic particles of conductive polymers such as polypirrole or polyacetylene and anisotropic aggregates of particles that are not anisotropic by themselves may also be used.

Examples of solvents include water, acetonitrile, ethers, dioxane, alcohols, aldehydes, ketones, esters, hydrocarbons, aromatics, preferably $C_1$–$C_{16}$, more preferably $C_1$–$C_{10}$, and mixtures thereof. Examples of alcohols include methanol, ethanol, isopropanol, perfluoropropanol, 1-butanol, 2-butanol, 2-butoxyethanol and octanol. Examples of aldehydes include formaldehyde, acetaldehyde, propionaldehyde, and glutaraldehyde. Examples of ketones include acetone, methylethylketone, and diethylketone. Example of esters include methyl acetate, ethyl acetate and phthalic acid butyl benzyl ester. Examples of hydrocarbons include hexane, heptane, octane, nonane, and decane, dichloromethane, chloroform, 1,1,1-trichloroethane, trichloroethylene, isophorone, 2-nitropropane, and tetrachloroethylene. Example of aromatics include benzene, toluene, xylene, 1,2,4-trimethylbenzene, phenol and naphthalene.

Examples classes of binders include polyalkylenes, polyalkylene glycols, polyalkylene alcohols, polyalkylene glycols, polyalkylene esters, and copolymers or mixtures thereof. Specific examples of binders include polyethylene, polypropylene, chlorinated polypropylene, polyvinyl alcohol, polyvinyl acetate, polyacrylate, polymethacrylate, cellulose polysaccharides, polystyrol, and mixtures or copolymers thereof.

The ink may be applied to a solid support and allowed to partially dry until ready for orientation. Example supports include paper, glass, metals and semiconductors, ceramics, polymers and plastics, polyethylene and other polyolephins, polyurethanes, polyvinyl chloride (PVC), polystyrene, polyesters, as well as knit, woven, and non-woven fibrous materials.

The readiness of the ink for orientation may be judged by the reflectivity of the ink surface. Freshly applied ink is glossy and flows easily. Partly dried, ready for orientation ink develops a scattering, thin, hazy layer on the surface. Concurrently, the viscosity of the ink increases. At this stage, the thin hazy layer is maintained on the ink surface during orientation. At too early a stage the surface remains glossy, and at too late a stage granulation develops on the surface of the ink, or the surface breaks, revealing glossy, wet ink and leads to macroscopic discontinuities in the ink trace. The optimal time period for orientation may be extended if the support carrying the partly dried ink is placed in a chamber containing a volatile solvent capable of permeating both the ink and support layers, for the example the solvent used in the ink itself. Examples of solvents fulfilling this criterion are ketones, (for example methylethyl ketone), alcohols (for example isopropanol and perfluoropropanol) or halogenated solvents (for example dichloromethane and carbon tetrachloride).

One method for orienting the particles in the ink is stretching the solid substrate 2 when the ink 1 is ready for orientation (FIG. 1). This will result in an increase of the specific conductivity of the ink trace proportional to the degree of stretching of the material. Examples of stretchable materials include polyolefins, PVC, polystyrene, polyesters, knit, woven and non-woven fibrous materials. Furthermore, some thermoplastic materials may be stretched if heated.

A successful stretching requires fluidity of the ink trace such that, at minimum, the stretching does not compromise the continuity of the conductor. Stretching initiated too early yields traces of specific conductivity equivalent to the original. Stretching initiated too late yields discontinuous traces. Stretching within the optimal time period yields a change in conductivity directly proportional to the stretching. For instance, stretching a polyethylene support by a factor of approximately 5.3. to 5.8 increases the conductivity of a graphite particulate ink trace by approximately a factor of 2.

Figure 2:
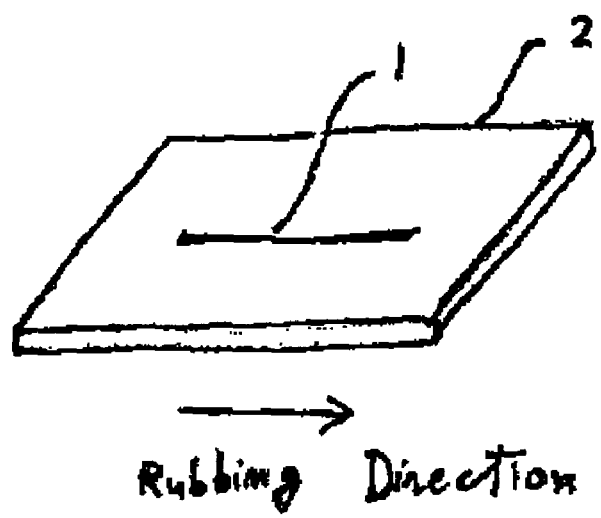
FIG. 2 illustrates the process of increasing the conductivity of an ink by rubbing.

In another method, the ink may be oriented by unidirectionally rubbing the surface of the partly-dried ink 1 with a soft or elastic material like rubber, latex, or a polyolefin, employing conditions that minimize unwanted smearing, until the desired conductivity is attained (FIG. 2). This technique is particularly useful when the support 2 is not stretchable.

Figure 3:
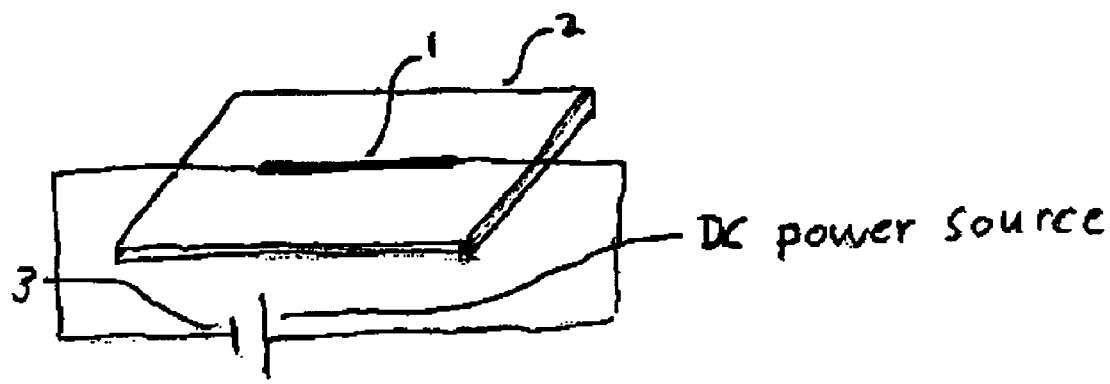
FIG. 3 illustrates the process of increasing the conductivity of an ink by electrical polarization.

Another method leading to increased conductivity is curing the ink by electrical polarization (FIG. 3). The leads of an electrical source 3, e.g. a battery, are connected to an ink trace 1, closing the circuit. The ink is allowed to dry, achieving the desired conductivity.

The particles in the ink may also be oriented by suspension in an orientable medium like a solvent or binder that promotes orientation of the particle during solvent evaporation. For instance, liquid crystals are known to promote the orientation of nanotubes (Abraham Harte, "Liquid crystals allow large-scale alignment of nanotubes", Caltech Undergraduate Research Journal, Vol 1, No 2, Nov. 30, 2001)). Thus, an ink that contains a liquid crystalline material, or goes through a liquid crystalline state during solvent evaporation, may orient the particles, thereby increasing conductivity during drying.

The methods described above may be used to manufacture, for example, electronic components, capacitors, circuit boards, electrodes, displays, and antistatic devices. Moreover, these methods are particularly useful for the manufacture of enzymatic electrochemical sensors. For example, a solution of an enzyme, and optionally one or more redox mediators, may be incorporated into the ink. Since no heat is required to cure the ink, the enzyme will not be denatured. This allows a simultaneous application of enzyme and ink together.

The resulting ink is applied to a substrate and cured with one or more of the methods of the invention. In an alternative approach, the enzyme, and optionally one or more mediators, is covalently bound to the particle as described in PCT Publication WO 96/06947. The resulting functionalized ink is then applied to a substrate, and cured with one or more of the methods of the invention.

Nanotubes are particularly useful for this application. They are highly conductive, anisotropic, and with a small cross-section. In addition, typical ink-jet printers require that the particulates must be small in order to avoid clogging the printer nozzle. Therefore, the use of nanotubes is particularly advantageous when a continuous ink-jet printer is used to print conductive ink traces. The conductivity of the trace thus printed is enhanced with one or more of the methods described above. Alternatively, the ink may be made more conductive by maintaining electrical continuity between the ink-jet outlet and the opposite end of the printed conductor, such that orienting electrical potential can be applied and maintained during drying of the ink. The electric field due to this electrical continuity orients the nanotubes in the drying ink.

In addition, new piezo continuous inkjet (CIJ) printers (Amir Noy, SGIA Journal, First Quarter 1999, pp. 31–33) can handle inks with large particulates that would clog the nozzles of typical inkjet printers. Thus, conductive inks containing carbon particles such as graphite or carbon fibers may also be used for printing and curing conducting ink traces.

The choice of the enzyme and optional mediator is dictated by the analyte to be quantified. For example, the enzyme may be horseradish or soybean peroxidase for hydrogen peroxide, laccase for oxygen, and glucose oxidase for glucose. Other examples of enzyme and mediator combination are reported below in Table A.

TABLE A

| Analyte | Enzymes | Mediator (Oxidized form) | Additional Mediator |
|---|---|---|---|
| Glucose | Glucose Dehydrogenase and Diaphorase | Ferricyanide | |
| Glucose | Glucose-Dehydrogenase | Ferricyanide | |
| Cholesterol | (Quinoprotein) Cholesterol Esterase and Cholesterol Oxidase | Ferricyanide | 2,6-Dimethyl-1,4-Benzoquinone 2,5-Dichloro-1,4-beuzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichioro-1,4-benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate Ferricyanide | |
| Lactate Dehydrogenase | Lactate Dehydrogenase and Diaphorase | Ferricyanide | Phenazine Ethosulfate or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

EXAMPLES

1) Quantifying the Effect of Substrate Extension on the Conductivity of Painted Graphite Wire.

An ink containing 20% colloidal graphite dissolved in isopropanol with small quantities of ketones and chlorinated hydrocarbons was painted in wires approximately 0.24 cm thick on a polyethylene substrate. The ink was left to partially dry and, before drying was complete, the substrate was stretched until the thickness of the wires had changed to approximately 0.08 cm. When appropriate, the drying of the ink was slowed down by the addition of a solvent, e.g. a higher alcohol like octanol. Untreated, reference wires were prepared in the same manner without the stretching step. The conductivity of the samples and references was measured in terms of wire resistivity (kW) per 3.3 cm of wire. Each experiment was performed in triplicate, and the mean values of reference and sample resistivity are reported in Table 1.

Table 1

2) Quantifying the Effect of Rubbing on the Conductivity of Painted Graphite Wire.

Graphite wires painted as described above were rubbed 20 times unidirectionally before complete drying of the solvent, with a neoprene glove. The resistivity of the wires was measured after 16 hours and compared to that of untreated reference wires of the same length and width. The experiment was carried out in duplicate and the results of each experiment are reported in Table 2a and Table 2b TABLE 2a

| Wire number | Resistivity of treated wire (k$\Omega \cdot$ cm) | Resistivity of reference untreated wire (k$\Omega \cdot$ cm) |
|---|---|---|
| 1 | 49 | 95 |
| 2 | 52 | 109 |
| 3 | 60 | 88 |
| 4 | 43 | 170 |
| 5 | 42 | 292 |
| 6 | 36 | 42 |
| 7 | 31 | 52 |
| 8 | 31 | 35 |
| 9 | 30 | 70 |

TABLE 2b

| Wire number | Resistivity of treated wire (k$\Omega \cdot$ cm) | Resistivity of reference untreated wire (k$\Omega \cdot$ cm) |
|---|---|---|
| 1 | 52 | 133 |
| 2 | 35 | 41 |
| 3 | 40 | 89 |
| 4 | 37 | 87 |
| 5 | 77 | 101 |
| 6 | 88 | 137 |

3) Quantifying the Effect of Electrical Polarization on the Conductivity of Painted Graphite Wire Nine graphite wire conductors, approximately 3.3 cm long and 0.16 cm wide, were painted on a glass substrate. Three wires were connected to the poles of a 9 Volt battery for 16 hours (FIG. 3), whereas the remaining six were left untreated. The treated conductors had a resistivity of 16.9, 18.7 and 24.3 k$\Omega$•cm respectively, and an average resistivity of 19.96 k$\Omega$•cm. The untreated wires had a resistivity of 42, 32, 33, 41, 65, 34 and k$\Omega$•cm respectively, and an average resistivity of 43.71 k$\Omega$•cm. Thus, the average treated to untreated conductivity ratio was 2.19:1.

4) Preparation of $H_2O_2$ Sensor with Graphite Ink and Horseradish Peroxidase.

Figure 4:
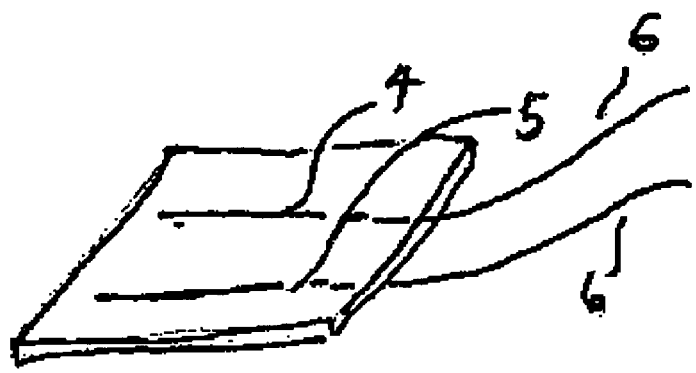
FIG. 4 illustrates the hydrogen peroxide sensor of Example 4.
Figure 5:
FIG. 5 illustrates a cyclic voltammetric scan obtained with the sensor pad of Example 4.

2 mL of graphite-based ink (20% colloidal graphite in a mixture of isopropanol, acetone, $CCl_4$, and minor quantities of other solvents) was mixed with 0.5 mL of horseradish peroxidase (a solution of 2 mg horseradish peroxidase in 1 mL of 0.1 M acetate buffer of pH 5.1). The resulting paint was used to coat sensing electrode tips (FIG. 4). The coating and a reference coating 5 were connected via leads 6 to an amperometric apparatus. Cyclic scanning voltammetry detected active horseradish peroxidase in the painted sensor pads. Incorporated horseradish peroxidase was sensitive to the presence of hydrogen peroxide in the electrochemical cell solution (FIG. 5).

5) Preparation of $H_2O_2$ Sensor with Graphite Ink, Pyrrole and Horseradish Peroxidase on a Metal Wire.

A silver/copper TEFLON® coated wire was cut and tipped with a carbon conductive ink and the ink cured at room temperature for 1 hour. The wire was immersed in a pH 5.1 acetate buffer, then, using platinum wire as the counter electrode and a W/WO$_3$ as the reference electrode, the wire was held at +2890 mV for 100 sec and at −110 mV for 200 sec. This served to polarize the surface. The wire was then immersed in a solution of 0.1 M pyrrole, 0.06 M KCl and 0.1 M acetate solution at pH 5.1 and the cell was run at +1790 mV for 100 sec. The resulting polypirrole-coated wire was put in a 0.1 pyrrole, 0.06 M KCl, 0.1 M acetate solution at pH 5.1 with 2 mg HRP per 1 ml of solution and run at +1790 mV for 90 cycles of 30,000 msec each. The electrode was then allowed to soak overnight in the same solution to increase HRP per unit surface area.

Figure 6:
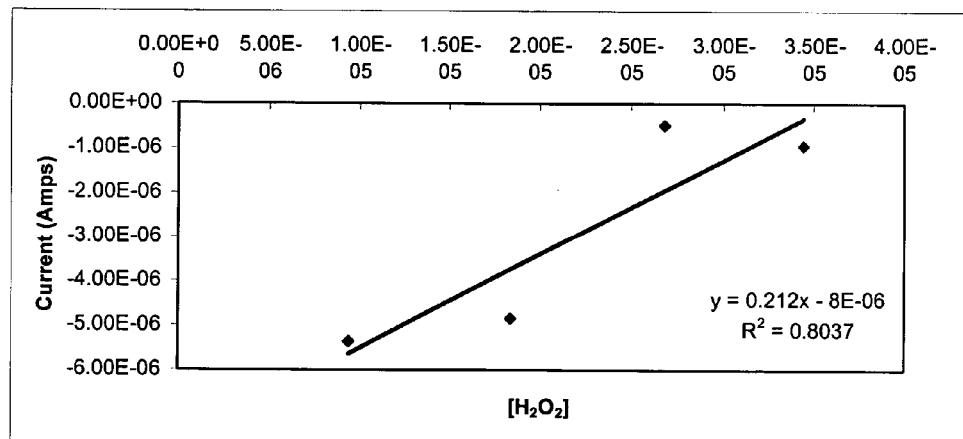
FIG. 6 illustrates the working curve of the sensor probe of Example 5.

The probe was tested at +840 mV with standardized solutions of H$_2$O$_2$ at different concentrations, obtaining a reliable working curve with the expected linear relationship of increasing current with increasing concentration (FIG. 6). The results of each experiment are reported in Table 3.

TABLE 3

| Experiment number | [H$_2$O$_2$] | Amps |
|---|---|---|
| 1 | 9.36E−06 | −5.37E−06 |
| 2 | 1.84E−05 | −4.85E−06 |
| 3 | 2.68E−05 | −4.88E−07 |
| 4 | 3.44E−05 | −9.46E−07 |

6) Prophetic Example. Preparation of Sensor with Nanotube Ink and Horseradish Peroxidase.

2 mL of saturated suspension of single-walled nanotube with a diameter between 12 and 15 nm (prepared according to the procedure of Zhu and Fan, J. Mater. Res., 1999, 14, 1175) in a mixture of isopropanol and acetone is mixed with 0.5 mL of horseradish peroxidase (a solution of 2 mg horseradish peroxidase in 1 mL of 0.1 M acetate buffer of pH 5.1). The resulting paint is used in a continuous ink-jet printer to print electrodes on an inert substrate. The conductivity of the printed electrodes is increased by one or more of the methods described above and/or by establishing electrical continuity between the ink-jet head and the opposite end of the printed ink. The resulting electrodes are used in sensors for determining the concentration of hydrogen peroxide.

7) Prophetic Example. Preparation of H$_2$O$_2$ Sensor with Pyrrole and Horseradish Peroxidase on a Cured Carbon Ink Wire.

A painted carbon ink wire is cured according to one of the methods described above. The tip of the cured wire is immersed in a pH 5.1 acetate buffer, then, using platinum wire as the counter electrode and a W/WO$_3$ as the reference electrode, the tip is held at +2890 mV for 100 sec and at −110 mV for 200 sec. This serves to polarize the surface. The wire is then immersed in a solution of 0.1 M pyrrole, 0.06 M KCl and 0.1 M acetate solution at pH 5.1 and the cell is run at +1790 mV for 100 sec. The resulting polypirrole-coated wire is put in a 0.1 pyrrole, 0.06 M KCl, 0.1 M acetate solution at pH 5.1 with 2 mg HRP per 1 ml of solution and run at +1790 mV for 90 cycles of 30,000 msec each. The electrode is then allowed to soak overnight in the same solution to allow HRP per unit surface area.

The invention claimed is:

1. A method of increasing conductivity of an ink, comprising:
   rubbing the ink to increase conductivity of the ink; followed by conducting electricity through the ink,
   wherein the ink comprises conductive non-spherical particles comprising carbon, and a solvent,
   the ink is on a substrate, and
   the method is carried out without curing at a temperature of at least 50° C. between the rubbing and the conducting.

2. The method of claim 1, wherein the ink further comprises a binder.

3. The method of claim 1, wherein the particles are selected from the group consisting of graphite, carbon fibers and nanotubes.

* * * * *

UNITED STATES PATENT AND TRADEMARK OFFICE
CERTIFICATE OF CORRECTION

| | | |
|---|---|---|
| PATENT NO. | : 7,097,788 B2 | Page 1 of 1 |
| APPLICATION NO. | : 10/610363 | |
| DATED | : August 29, 2006 | |
| INVENTOR(S) | : Ewa Stanislawa Kirkor | |

It is certified that error appears in the above-identified patent and that said Letters Patent is hereby corrected as shown below:

On the Title Page - (75) Inventors:

After "Kirkor" please delete "Bradford" and insert --Branford--.

Signed and Sealed this

Thirteenth Day of November, 2007

JON W. DUDAS
*Director of the United States Patent and Trademark Office*